(12) United States Patent
Avila et al.

(10) Patent No.: US 12,150,664 B2
(45) Date of Patent: Nov. 26, 2024

(54) ADJUSTABLE LOCKING HANDLE DESIGN FOR DEBRIDERS

(71) Applicant: GYRUS ACMI, INC., Westborough, MA (US)

(72) Inventors: I. Miroslava Avila, Bristol, CT (US); Jeffrey Radziunas, Wallingford, CT (US)

(73) Assignee: Gyrus ACMI, Inc., Westborough, MA (US)

( * ) Notice: Subject to any disclaimer, the term of this patent is extended or adjusted under 35 U.S.C. 154(b) by 138 days.

(21) Appl. No.: 17/650,316

(22) Filed: Feb. 8, 2022

(65) Prior Publication Data

US 2022/0249114 A1 Aug. 11, 2022

Related U.S. Application Data (60) Provisional application No. 63/147,732, filed on Feb. 9, 2021.

(51) Int. Cl.
*A61B 17/00* (2006.01)
*A61B 17/32* (2006.01)
*A61B 17/29* (2006.01)

(52) U.S. Cl.
CPC ............. *A61B 17/32002* (2013.01); *A61B 2017/00398* (2013.01); *A61B 2017/0046* (2013.01); *A61B 2017/320004* (2013.01); *A61B 2017/320028* (2013.01)

(58) Field of Classification Search
CPC ...... A61B 17/32002; A61B 2017/0046; A61B 2017/00367; A61B 2017/00398; A61B 2017/00407; A61B 2017/2925; A61B 2017/291; A61B 2017/320004; A61B 2017/320028; A61B 17/2841; A61B 17/2909; A61B 2017/2941
See application file for complete search history.

(56) References Cited

U.S. PATENT DOCUMENTS

| | | | |
|---|---|---|---|
| 7,328,752 B2 * | 2/2008 | Gass | B23B 49/008 173/217 |
| 8,998,887 B2 | 4/2015 | Simmen et al. | |
| 2011/0301577 A1 | 12/2011 | Simmen et al. | |
| 2019/0175220 A1 * | 6/2019 | Coppedge | A61B 17/1671 |

(Continued)

FOREIGN PATENT DOCUMENTS

WO    WO-9724072 A1    7/1997

OTHER PUBLICATIONS

"European Application Serial No. 22151413.6, Extended European Search mailed Jun. 10, 2022", 5 pgs.

(Continued)

*Primary Examiner* — Phong Son H Dang
*Assistant Examiner* — Lindsey R. Rivers
(74) *Attorney, Agent, or Firm* — Schwegman Lundberg & Woessner, P.A.

(57) ABSTRACT

A medical device for debridement can include a handpiece, a shaft extending through the handpiece and distally therefrom, a drive to manipulate the cutter, a handle slidably coupled to the elongate housing and extending distally therefrom, and at least one locking mechanism configured to fix the handle to the handpiece. The handle can be configurable to multiple positions along the length of the handpiece, and can be removed therefrom.

6 Claims, 10 Drawing Sheets

(56) References Cited

U.S. PATENT DOCUMENTS

2019/0201068 A1\* 7/2019 Jones ................. A61B 17/162
2020/0330105 A1\* 10/2020 Bornhoft ............... A61B 90/03
2020/0330106 A1 10/2020 Bornhoft et al.

OTHER PUBLICATIONS

"European Application Serial No. 22151413.6, Response filed Jan. 7, 2023 to Extended European Search mailed Jun. 10, 2022", 15 pgs.
"European Application Serial No. 22151413.6, Communication Pursuant to Article 94(3) EPC mailed Oct. 27, 2023", 4 pgs.

\* cited by examiner

ADJUSTABLE LOCKING HANDLE DESIGN FOR DEBRIDERS

CROSS-REFERENCE TO RELATED APPLICATION

This application claims the benefit of priority to U.S. Provisional Patent Application Ser. No. 63/147,732, filed Feb. 9, 2021, the content of which is hereby incorporated by reference in its entirety.

TECHNICAL FIELD

This document pertains generally, but not by way of limitation, to devices and methods for debridement.

BACKGROUND

In a medical procedure, such as debridement, a medical device can be used such as to remove portions of tissue, bone, and/or other objects from a surgical site. The medical device can be a shaver, a debrider, a microdebrider, morcellator, or other suitable device for debridement. The medical device can have a cutting portion extending from a housing. During the procedure, the housing can be held by a professional and positioned relative to a patient such as to provide precise and careful removal of objects. Modern debriders can incorporate various minimally intrusive cutting mechanisms to shorten recovery time from the procedure. In such minimally intrusive cutting mechanisms, the cutter can be partially enclosed such as to only allow for cutting in a small window of the cutting mechanism. A shaft supplying the cutter can also be curved such as to enable further precision. Axial rotation of the elongated housing of the medical device can alter the direction of a cutting window and/or the angle of the cutting portion.

SUMMARY

In an approach to debridement, a medical device can be used such as to abrade and remove portions of tissue or other objects. A medical device can have a cutting mechanism which can be rotatable relative to a housing by manipulation of a nosecone. One example of a medical device can have a housing without a handle and can be gripped by the professional like a pen between a thumb, index finger, and middle finger. Some professionals can prefer pen grip for certain placements and procedures of debridement. Another example of a medical device can have a housing connected to a handle and can be gripped by the professional like a pistol. Some professionals can prefer the pistol grip for certain placements and procedures of debridement and can utilize the ergonomic ease of manipulating the nosecone while the housing is securely anchored by hold of the handle.

Optimal grip of the device can vary among professionals across procedures depending on user hand size and shape, user technique, surgical site location, and other factors. The present inventors have recognized, among other things, that the limited available grip orientations available to a user of a medical device can create the need to alternate between multiple devices or can cause the professional to undertake the procedure without optimal ergonomic position of the device.

Aspect 1 can include or use a medical device for tissue removal, and the medical device can include or use an elongate housing, a shaft extending through the elongate housing and distally therefrom, the shaft containing a cutter configured to sever tissue, a drive configured to rotate the cutter, reciprocate the cutter, or both, a handle slidably coupled to the elongate housing and extending distally therefrom, and at least one locking mechanism configured such as to fix the handle to the elongate housing at a plurality of different longitudinal positions along the elongate housing. In Aspect 2, the medical device of Aspect 1 can optionally be configured such that the handle can be detachable from the elongate housing. In Aspect 3, the medical device of Aspect 1 and/or Aspect 2 can be optionally configured such that the handle can be slidably coupled to at least one longitudinal groove of the elongate housing. In Aspect 4, the medical device of any one or any combination of Aspects 1-3 can optionally be configured such that the handle can be configured such as to provide an unlocked position wherein the handle can slide within the at least one longitudinal groove, and a locked position wherein the locking mechanism can apply pressure to the elongate housing, the pressure restricting travel of the handle relative to the housing. In Aspect 5, the medical device of any one or any combination of Aspects 1-4 can optionally be configured such that the locking mechanism can include or use a moveable element slidable within a bore of the handle, the moveable element configured such as to protrude from the bore distally towards the elongate housing and apply pressure thereto. In Aspect 6, the medical device of any one or any combination of Aspects 1-5 can optionally be configured such that the moveable element can be configured to be manipulated by a lever mechanism to protrude from the bore. In Aspect 7, the medical device of any one or any combination of Aspects 1-6 can optionally be configured such that the moveable element can be configured such as to be manipulated by a screw mechanism to protrude from the bore. In Aspect 8, the medical device of any one or any combination of Aspects 1-7 can optionally be configured such that the at least one longitudinal groove can be a t-shaped slot. In Aspect 9, the medical device of any one or any combination of Aspects 1-8 can optionally be configured such that a t-shaped nut is attached at a protruding end of the moveable element, the t-shaped nut configured such as to apply pressure to the t-shaped slot upon manipulation of the element by the cam. In Aspect 10, the medical device of any one or any combination of Aspects 1-9 can optionally be configured such that the locking mechanism can be configured such as to apply medial pressure on two or more longitudinal grooves of the elongate housing. In Aspect 11, the medical device of any one or any combination of Aspects 1-10 can optionally be configured such that each of the longitudinal grooves can include or use a plurality of detents. In Aspect 12, the medical device of any one or any combination of Aspects 1-11 can optionally be configured such that the handle can include or use two or more detent balls configured such as to apply medial pressure on the two or more longitudinal grooves. In Aspect 13, the medical device of any one or any combination of Aspects 1-12 can optionally be configured such that each of the detent balls can be sized and shaped such as to be at least partially disposed within one of the plurality of detents. In Aspect 14, the medical device of any one or any combination of Aspects 1-13 can optionally be configured such that longitudinal travel of the handle relative to the elongate body can be restricted while each of the detent balls of the handle are at least partially disposed within one of the plurality of detents. In Aspect 15, the medical device of any one or any combination of Aspects 1-14 can optionally be configured such that the handle can include or use a handle base, a pair of jaws hingedly connected to the handle base, and a sleeve configured to move the pair of jaws medially to a closed position, wherein the handle can be configured such as to grasp the elongate housing in the closed position. In Aspect 16, the medical device of any one or any combination of Aspects 1-15 can optionally be configured such that the pair of jaws can each be biased such as to hinge laterally from the elongate housing. In Aspect 17, the medical device of any one or any combination of Aspects 1-16 can optionally be configured such that manual movement of the sleeve distally from the elongate housing can allow the pair of jaws to move laterally from the elongate housing to an open position. In Aspect 18, the medical device of any one or any combination of Aspects 1-17 can optionally be configured such that the sleeve can be biased to move distally towards the device, and the sleeve can cause the pair of jaws to hinge medially to the closed position. In Aspect 19, the medical device of any one or any combination of Aspects 1-18 can optionally be configured such that the sleeve can be configured to move distally from the elongate housing upon manual rotation of the sleeve. In Aspect 20, the medical device of any one or any combination of Aspects 1-19 can optionally include or use a sleeve lock configured such as to hold the sleeve proximal to the elongate housing, and the sleeve can restrict the pair of jaws from hinging laterally to the open position. Each of these non-limiting examples can stand on its own, or can be combined in various permutations or combinations with one or more of the other examples.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

DETAILED DESCRIPTION

The present disclosure, in one or more embodiments, relates to devices and methods for surgical debridement. More particularly, the present disclosure relates to an adjustable debrider and methods for versatile and precise debridement. A debridement procedure can be undergone to remove dead, damaged, necrotic, or infected tissue or other objects from a surgical site. A medical device such as a debrider, multidebrider, microdebrider, shaver, or other device can be utilized for selective, minimally invasive debridement. Debridement can be used to remove bone or tissue in ear, laryngeal, paranasal, nasal, uterine, tonsil, adenoid, and skull base surgeries. Debridement can also be used for other beneficial surgical purposes and at other surgical sites.

A debrider can include or use a handpiece, referred to herein as an elongate housing, which can be coupled to a shaft, also referred to herein as a blade. The debrider can be connected to other elements in a debridement system, such as a power supply, suction supply, irrigation line, motor control unit, declog valves, or other elements. The debrider can function to cut, shave, or drill material from a surgical site and can facilitate aspiration of the material from the site and to a collection cannister or other destination. The blade can be removably coupled to the housing and can be sized and shaped according to the specific surgical site. Accordingly, a professional can interchangeably couple one of a wide variety of blades to the housing depending on the procedure at hand. Depending on the size and shape of the blade and the surgical site, a professional can alter technique and grip in using the debrider. The housing can also be sized and shaped according to a preferential technique of a professional or to accommodate operation at a specific site. One approach to debridement is to use a completely disposable device manufactured for specific use at a particular site. This disposable device can have a handle fixed at a predetermined position on the housing. A problem with that approach, however, is that a professional cannot make adjustments to handle placement or employ several holds on the device during the procedure. As such, the professional can be inhibited from dynamically altering their technique to meet the needs of the procedure at hand. The present devices and techniques can help avoid such problems because the device is easily and quickly adjustable to several configurations.

The present disclosure relates to, among other things, a device and method enabling debridement at multiple surgical sites. The device also can help reduce the number of exchanges of medical devices during a procedure and can increase ease and precision of debridement by a professional. The device can be configured to be held by a professional during debridement using any of several common techniques. Additionally, the device can be configured to be held by an adjustable, removable handle. Alternatively or additionally, the device can be configured to be held by the device housing, and the handle can be easily removed from the device such as to remain out of the way for pen grip. The device can be configured to allow for various secure holding positions of the device with a dominant hand and ergonomic rotation of a nosecone with a non-dominant hand. Further, the device can be configured to allow for multiple points of connection of the handle along the length of the housing.

Figure 1:
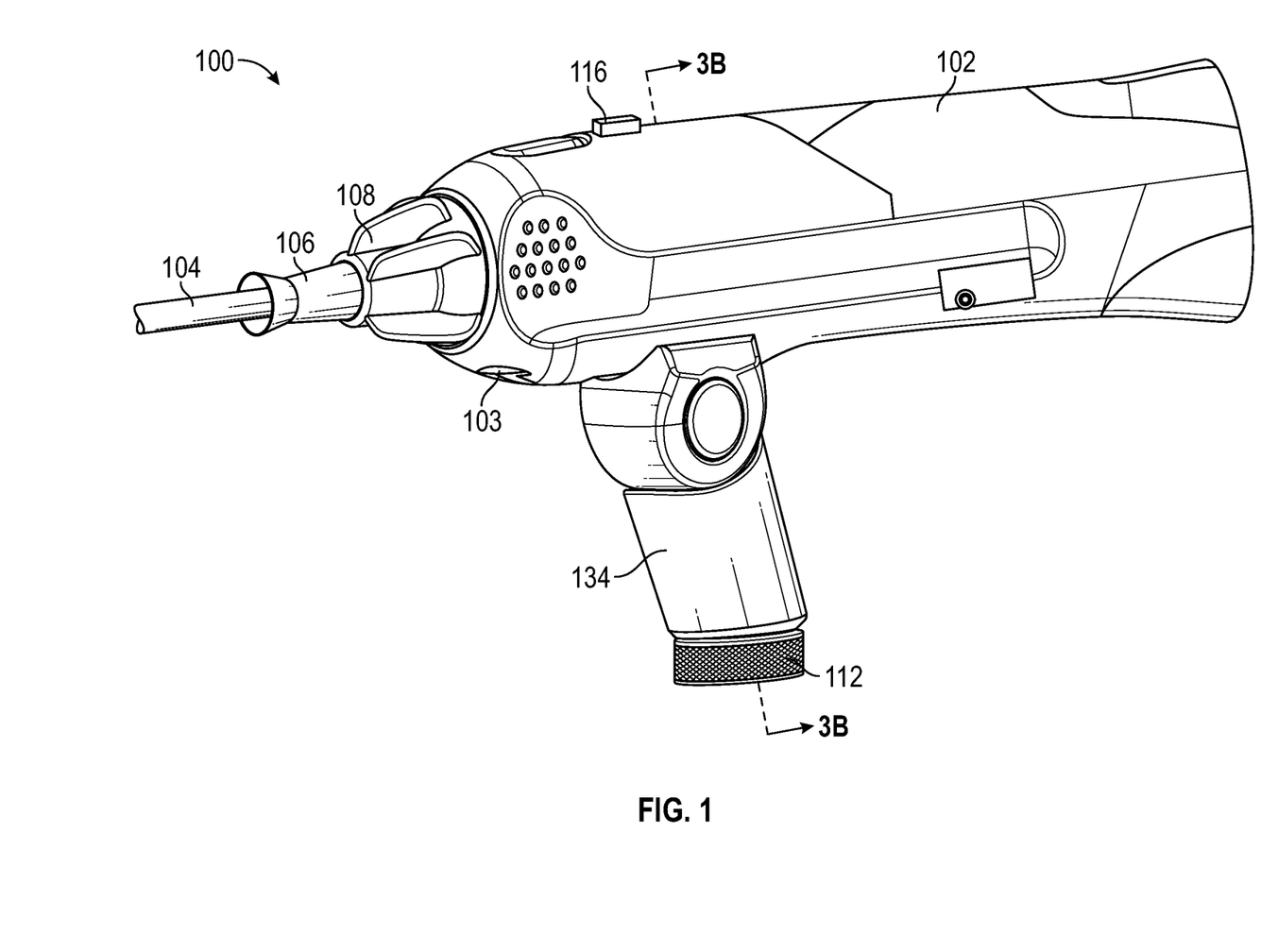
FIG. 1 is a perspective view of a debrider.

FIG. 1 shows a perspective view of an example of a debrider. A debrider 100 can include or use an elongate housing 102, a blade 106, a cutter 104, a nosecone 108, and an actuator 116. The housing 102 can be elongate and can be substantially cylindrically shaped. The housing 102 can also be substantially elliptically, cylindrically shaped. Diameters of housings 102 shaped as such can be within a range of about 0.25 inches to about 2 inches. In some examples, the housing diameters can be within the range of about 0.875 inches to about 1.25 inches. The housing 102 can be reusable, such as can be washable or autoclavable. Alternatively, the housing 102 can be disposable, its inner contents configurable to a new housing. The debrider 100 can also include or use a handle 134 coupled to the housing 102. The handle 134 can be intended for removal from the housing 102 once it has been coupled. The handle can be able to be removed from the housing 102 without excessive force or breakage once it has been coupled. The handle 134 can include or use an adjustment knob 112. The handle can be sized and shaped such as to pair with a longitudinal channel or slot 103 of the housing 102. The blade 106 can be attached or coupled to the housing 102 and extend therefrom. The blade 106 can extend at least partially through the housing 102. The blade 106 can include or use a cutting mechanism, referred to herein as cutter 104. The blade 106 can be curved at a variety of different angles such as to allow for precision in placement of the cutter 104 during debridement. The cutter 104 can be a reciprocating or oscillating pair of cutting members, a rotating cutting member, or both. Alternatively or additionally, the cutter 104 can be a rotating burr. The cutter 104 can also be an electrode cutter. An illustrative example of an electrode cutter is described in U.S. patent application Ser. No. 15/936,678, filed on Mar. 27, 2018, and entitled Electrode Blade for Shavers, which is incorporated by reference herein in its entirety, including for its teaching of a medical device having an electrode blade, which can be used in combination with the debridement device described in the present disclosure. The cutter 104 can also include or use other mechanisms suitable for debridement blades. The cutter can include a cutter window such as to focus the cutting action in a particular lateral direction relative to the blade 106. The housing can include or use a blade drive mechanism configured to drive the cutter 104. The blade drive mechanism can be an electric motor, a solenoid assembly, or other appropriate mechanism to move the cutter 104. For example, the cutter 104 can be motorized. The blade drive mechanism can be activated by an actuator 116. The actuator 116 can be a switch, a knob, a button, or other mechanism for actuation of the cutter 104. The actuator 116 can be located on the housing 102, such as located on the top of the housing as depicted in FIG. 1. The actuator 116 can be located at other locations on the housing, or alternatively or additionally can be located at a remote location, such as on a footswitch. The blade 106 can include or use a nosecone 108 at or near a blade connection point at a distal end of the housing 102. Turning the nosecone 108 about a medial axis of the housing 102 can cause rotation of the blade 106. Where the cutter 104 of the blade 106 has a cutter window, turning of the nosecone 108 can alter the lateral direction of the cutter window. Further, where the blade 106 is curved at an angle, turning of the nosecone 108 can alter the lateral direction in which the angled blade 106 extends. The debrider 100 can be itself a component of a larger debridement system. For example, the debrider can be tethered to a source of suction, irrigation, or both via one or more connection lines 142 (see FIGS. 2A and 2B). Accordingly, the debrider 100 can provide aspiration and removal of tissue and other objects as they are shaved, cut, or drilled. For example, the debrider 100 can contain a port configured to supply remote suction and/or irrigation to a lumen of the blade or shaft 106. Aspiration can be a helpful feature of a debrider 100 with respect to cutting performance.

Figure 2A:
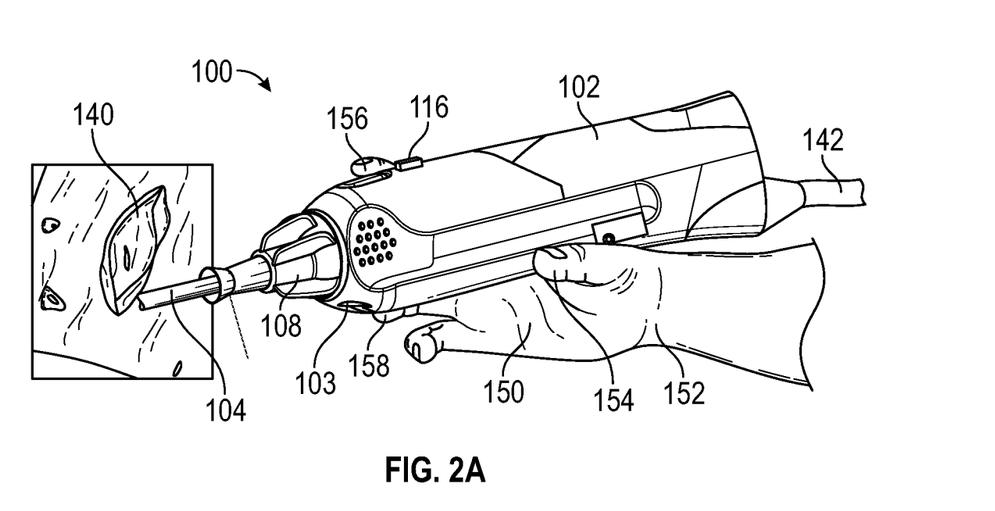
FIG. 2A is a side view of a debrider in operation with a pen grip.

FIG. 2A shows a side view of an example of a debrider in operation with a pen grip. A professional can hold or grasp the debrider 100 by the housing for certain procedures and techniques. Generally, such a hold can be referred to as "pen grip". FIG. 2A shows one way a professional can use the debrider 100 in pen grip. The housing 102 can rest at or near a dominant hand 150 between a thumb 154 and an index finger 156. While distinguished herein as the dominant hand 150 and the non-dominant hand, it is understood that either hand can be interchangeably used. The housing 102 can also rest at or near the middle finger 158, as shown. The professional can securely grip the housing between the thumb 154 and index finger 156 and further anchor the hold by gripping the housing 102 with the middle finger 158. Other fingers, such as a ring finger or pinky finger can also be used to grip the housing 102 in pen grip. Pen grip can enable a professional to have enhanced control and placement of the cutter 104 relative to the surgical site 140. For instance, pen grip can enable secure, ergonomic rotation of the debrider 100 without excess strain on a wrist 152. Pen grip can further be advantageous for certain techniques and procedures depending on the professional's facility, hand size, and other factors. It can also be used to accommodate various individual patient anatomies and pathologies. For pen grip, the handle (as depicted in FIG. 1) can be removed. The debrider 100 can be used in pen grip without the handle 134 extending distally from the housing 102 such as to avoid interference of the handle 134 during the procedure.

Figure 2B:
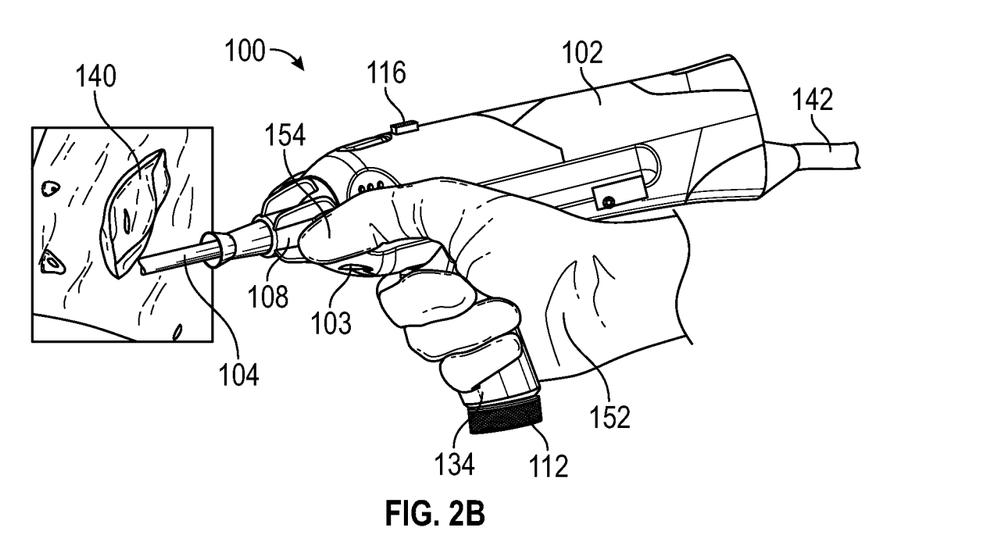
FIG. 2B is a side view of a debrider in operation with a pistol grip.

FIG. 2B shows a side view of an example of a debrider in operation with a pistol grip. A professional can hold or grasp the debrider 100 by the handle 134. Generally, such a hold can be referred to as "pistol grip". FIG. 2B shows one way a professional can use the debrider 100 in pistol grip. The handle 134 can extend distally from the housing 102 such as to allow for the debrider 102 to be held solely by the handle 134. A professional can also hold the debrider holding the handle 134 and the housing 102. In one example of a hold depicted in FIG. 2B, a professional can securely grab the handle 134 between the thumb 154 and fingers, the handle 134 being held in an arch of the hand 150. Other techniques of holding the handle 134 can be used. Pistol grip can provide a professional with enhanced power and stability in using the debrider 100. Pistol grip can also enable ergonomic rotation of the nosecone 108 relative to the housing 102 using the non-dominant hand, such as to allow for secure, anchored counterforce applied by the dominant hand 150. Using the nosecone 108 (rather than rotating the housing 102) to rotate the cutter 104 can be beneficial for certain procedures as the housing 102 is generally tethered to the one or more connection lines 142. Pistol grip can further be advantageous for certain techniques and procedures depending on the professional's facility, hand size, and other factors. It can also be used to accommodate various individual patient anatomies and pathologies. The handle 134 can include or use mechanisms such as to allow for variable longitudinal placement of the handle 134 relative to the housing 102. Variable longitudinal placement of the handle 134 can be available in predefined increments, such as by incremental indentations or protrusions on the housing 102. Alternatively, variable longitudinal placement of the handle can be available continuously along the housing 102. The handle 134 can include or use one of several locking mechanisms to fix the handle 134 to the housing at a plurality of different longitudinal positions along the housing 102. The handle 134 can extend distally from the housing 102 at a length within a range of about 0.2 inches to about 6 inches. In some examples, the handle 134 can extend at a length within the range of about 2 inches to about 3.5 inches.

Figure 3A:
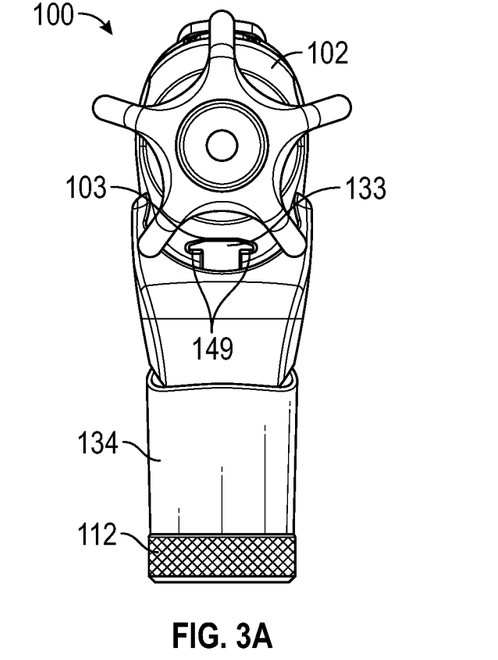
FIG. 3A is a front view of a handle paired to a debrider.
Figure 3B:
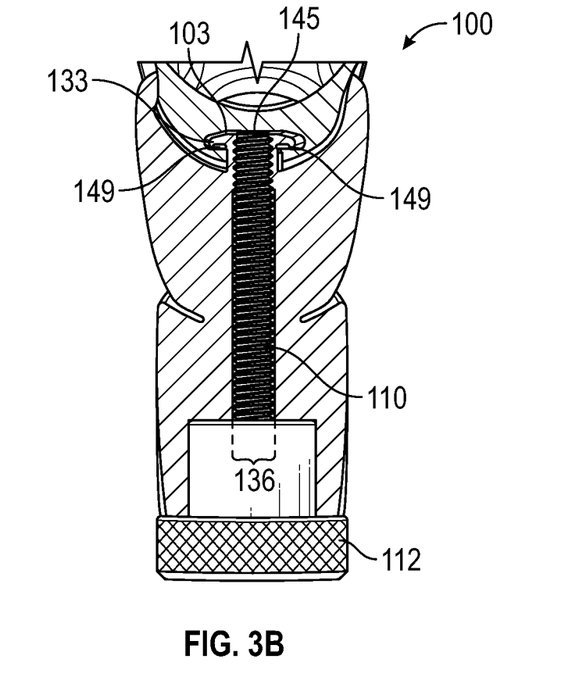
FIG. 3B is a cross-section view of a handle paired to a debrider.

FIG. 3A shows a front view of an example of a handle paired to a debrider. A handle 134 can include or use a knob 112, a rod 110 (as depicted in FIG. 3B), a tongue 133, and one or more tongue grips 149. The housing 102 of the debrider 100 can include or use a channel or slot 103 located on the underside of the housing 102. The slot 103 can be a t-shaped slot. The slot 103 can also be triangular shaped, or can be otherwise shaped for coupling in a similar manner. The handle 134 can be sized and shaped such that the tongue 133 can mate to the slot 103 of the housing 102. As such, the tongue 133 can be a t-shaped tongue. The tongue 133 can also be triangular shaped, or can be otherwise shaped for coupling in a similar manner. The tongue can include or use one or more tongue grips 149. FIG. 3A depicts a pair of tongue grips 149 located on the underside of a t-shaped tongue 133. The tongue grips 149 can be located between the tongue 133 and the slot 103 and can function to increase friction between the two. The tongue grips can also be located in the slot 103 of the housing, or located on both the tongue 133 and the slot 103. The tongue grips 149 can be members made of rubber, plastic, metal, or other suitable material for providing friction. The tongue grips 149 can also be a surface finish on either or both of the tongue 133 and slot 103. For example, the tongue grips 149 can be knurling, serrations, or other finish on the surface of the tongue 133, slot 103, or both. While the slot 103 is described herein being located on the housing 102 and sized and shaped to mate with the tongue 133 located on the handle 134, it is also understood that the slot 103 can be located on the handle 134 and the tongue 133 on the housing and can function similarly.

Figure 3C:
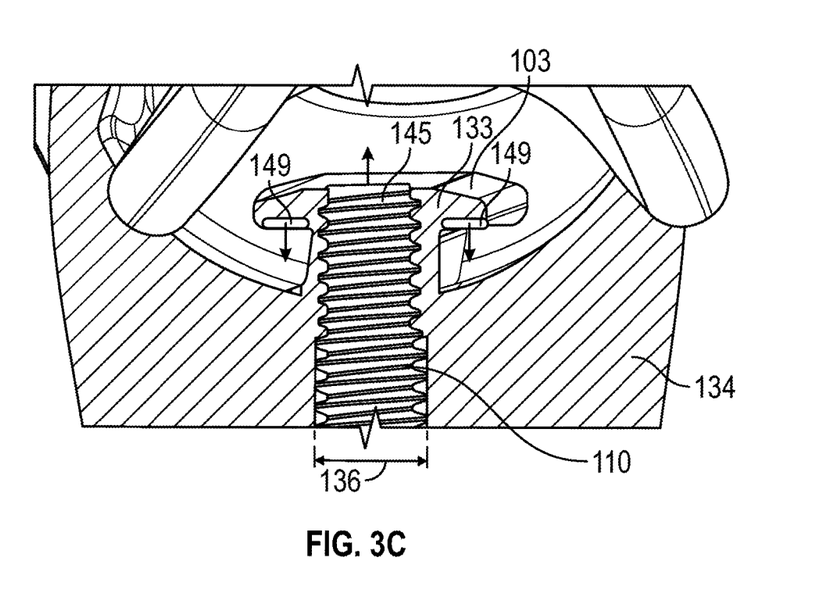
FIG. 3C is an isolated cross-section view of a handle paired to a debrider.

FIG. 3B shows a cross-section view of an example of a handle paired to a portion of a debrider. Here, the cross-section view of the portion of the debrider 100 is taken along a plane 3B-3B as shown in FIG. 1. The knob 112 can be attached to the rod 110 which extends through a bore 136 of the handle 134. The rod 110, which can be threaded as depicted in FIGS. 3B & 3C, can attach by screwing to a threaded hole of the knob 112. Alternatively or additionally, the rod 110 can be attached to the knob 112 such as with an ultraviolet-curable adhesive. The rod 110 can also be bonded to the knob 112 such as with the use of radiofrequency welding, solvent, or glue. Other suitable methods of attachment can also be used. Both the rod 110 and the bore 136 can be threaded complementarily such that the rod 110 can be screwed into the bore 136. Turning the knob 112 can cause the rod 110 to protrude out the bore 136 proximally towards the housing 102. Turning the knob 112 can cause the rod 110 to be retracted into the bore distally away from the housing 102.

FIG. 3C shows an isolated cross-section view of an example of a handle paired to a debrider. When the tongue 133 is mated to the slot 103, the handle 134 can be slidably connected to the housing 102. When the knob 112 is turned to cause the rod 110 to protrude out the bore 136 proximally towards the housing, a superior end 145 of the rod 110 can contact slot 103 of the housing 102. Protrusion of the rod 110 can create pressure between the housing 102 and the handle 134, causing the tongue 133 to be pressed distally away from the housing 102. Thus, protrusion of the rod 110 can compress the tongue grips 149 against the slot 103, such as against rails of the slot 103. Similar compression can occur where the tongue grips 149 are located in the slot 103. Where the tongue grips 149 are compressed between the slot 103 and the tongue 133, longitudinal sliding of the handle 134 relative to the housing 102 can be restricted. Turning the knob 112 an opposite direction can cause the rod 110 to retract into the bore 136 distally away from the housing 102. Releasing the rod 110 pressure on the slot 103 can cause decompression of the tongue grips 149 and restore free longitudinal movement of the handle 134 relative to the housing 102.

In operation and use, a professional can provide or obtain a medical device 100 for use in debridement. The professional can turn the knob 112 of the handle 134 in a locking direction to clamp the handle 134 to the housing 102, restricting longitudinal motion of the handle 134 relative to the housing 102. The professional can turn the knob 112 of the handle 134 in an unlocking direction to restore longitudinal motion of the handle 134 relative to the housing 102. In one example, the professional can turn the knob 112 in the unlocking position, unclamping the handle 134, and can slidably remove the handle 134 from the housing 102 and use the device in "pen grip". In another example, the professional can secure the handle 134 to a desired longitudinal position of the housing 102 by turning the knob 112 in a locking direction and use the device in "pistol grip". The professional can position the cutter 104 relative to the surgical site 140, and sever, cut, shave, drill, and/or remove tissue or other objects therefrom.

Figure 4A:
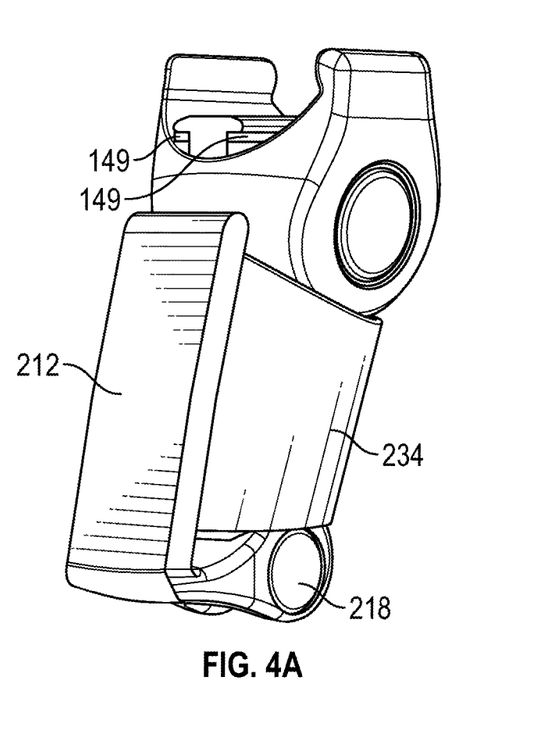
FIG. 4A is a perspective view of a debrider handle in a locked position.
Figure 4B:
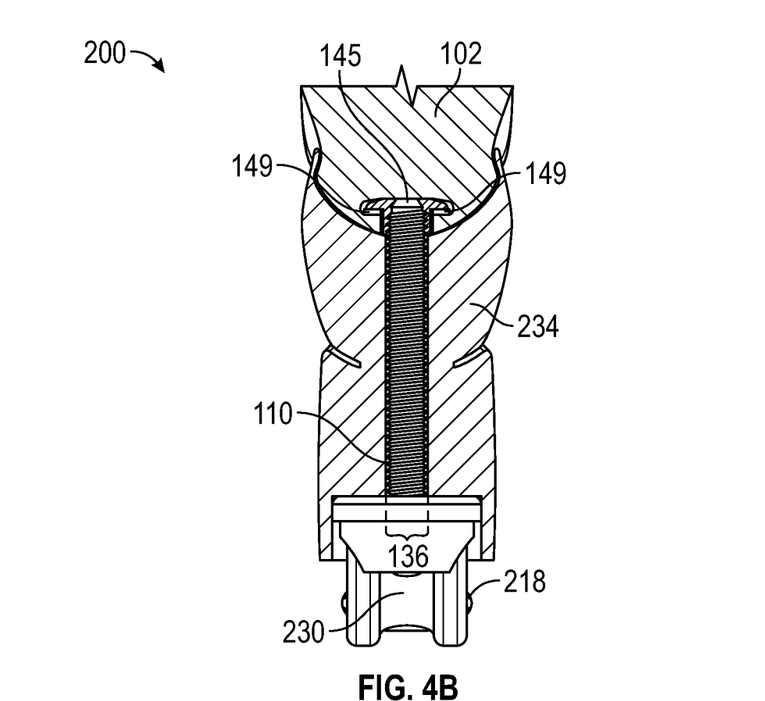
FIG. 4B is a cross-section view of a handle paired to a debrider.
Figure 4C:
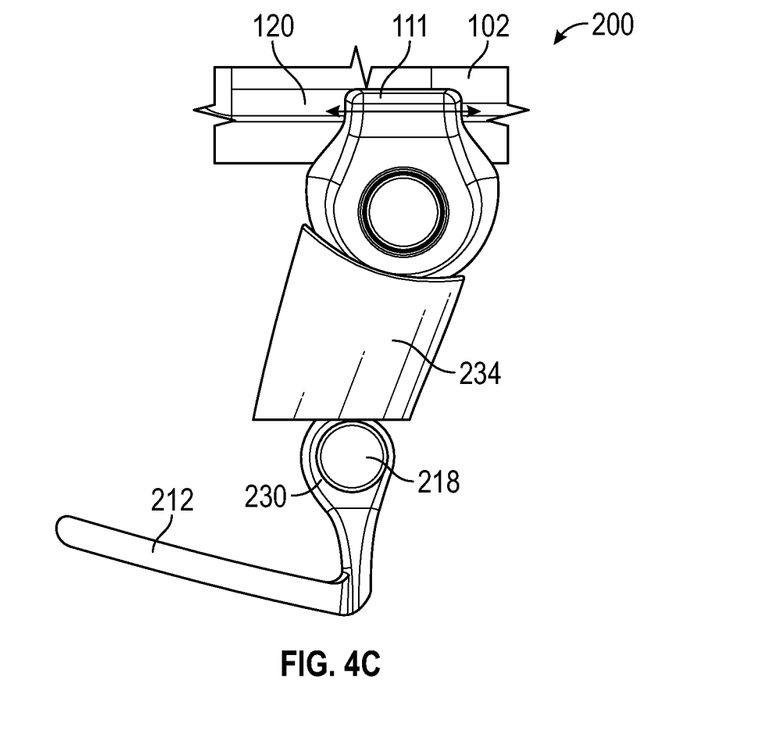
FIG. 4C is a side view of a handle paired to a debrider in an unlocked position.

FIGS. 4A-4C show another example of a debrider handle. Particularly FIG. 4B shows a cross-section view of an example of a handle paired to a portion of a debrider. Here, the cross-section view of the portion of the debrider 100 is taken along a plane 3B-3B as shown in FIG. 1. Handle 234 is similar to handle 134, but contains a lever 212 connected to the handle 234 about a pivot 218. The pivot 218 can be a pin, rod, or other substantially cylindrical portion extending through the handle 234 and the lever 212. The pivot 218 can also be a physical, rotatable connection between the body of the lever 212 and the handle 234. The pivot 218 can also be one or more projections on the handle 234 which can mate with one or more apertures on the lever 212. The pivot 218 can also be one or more projections on the lever 212 which can mate with one or more apertures on the handle 234. The lever 212 can be connected to the handle 234 eccentrically about the pivot 218 such that a cam 230 is created about the pivot 218. The cam 230 can be attached to the rod 110, such as can attach by screwing to a threaded hole of the cam 130. Alternatively or additionally, the rod 110 can be attached to the cam 130 such as with an ultraviolet-curable adhesive. The rod 110 can also be bonded to the cam 130 such as with the use of radiofrequency welding, solvent, or glue. Other suitable methods of attachment can also be used. The cam 130 can be oriented eccentrically such as to convert rotational motion from the lever 212 to linear motion of the rod 110 within the bore 136. Turning or closing the lever 212 radially about the pivot 218 towards the handle 234 can cause the cam 130 to manipulate the rod 110 to protrude out the bore 136 to contact the housing, compressing the tongue grips 149 against the slot 103, such as against rails of the slot 103. Similar compression can occur where the tongue grips 149 are located in the slot 103. Where the tongue grips 149 are compressed between the slot 103 and the tongue 133, longitudinal sliding of the handle 234 relative to the housing 102 can be restricted. Thus, when the lever 212 is turned completely to a locked position, as depicted in FIG. 4A, the handle 234 can be secured to a desired position along the length of the housing 102. Releasing the lever 212 from the locked position can cause the rod 110 to retract into the bore 136 distally away from the housing 102. Releasing the lever to an unlocked position, as depicted in FIG. 4C, can cause decompression of the tongue grips 149 and restore free longitudinal movement of the handle 234 relative to the housing 102.

In operation and use, a professional can provide or obtain a medical device 200 for use in debridement. The professional can radially turn the lever 212 of the handle 234 to the locked position to clamp the handle 234 to the housing 102, restricting longitudinal motion of the handle 234 relative to the housing 102. The professional can radially turn the lever 212 of the handle 234 to the unlocked position to restore longitudinal motion of the handle 234 relative to the housing 102. In one example, the professional can radially turn the lever 212 to the unlocked position, unclamping the handle 234, and can slidably remove the handle 234 from the housing 102 and use the device in "pen grip". In another example, the professional can secure the handle 234 to a desired longitudinal position of the housing 102 by radially turning the lever 212 to the locked position and use the device in "pistol grip". The professional can position the cutter 104 relative to the surgical site 140, and sever, cut, shave, drill, and/or remove tissue or other objects therefrom.

Figure 5A:
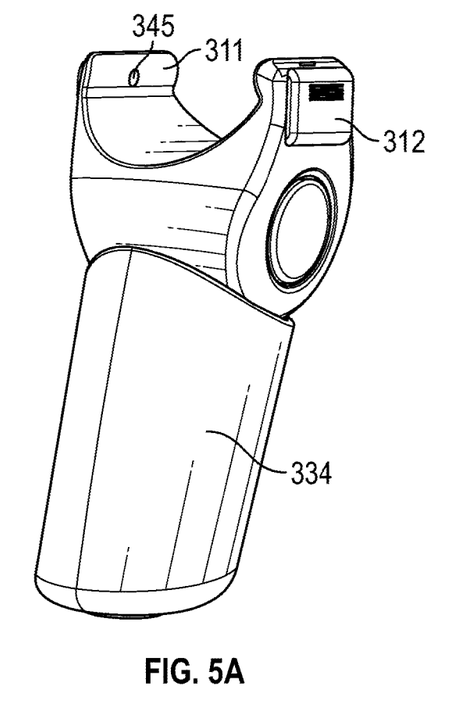
FIG. 5A is a perspective view of a debrider handle.
Figure 5B:
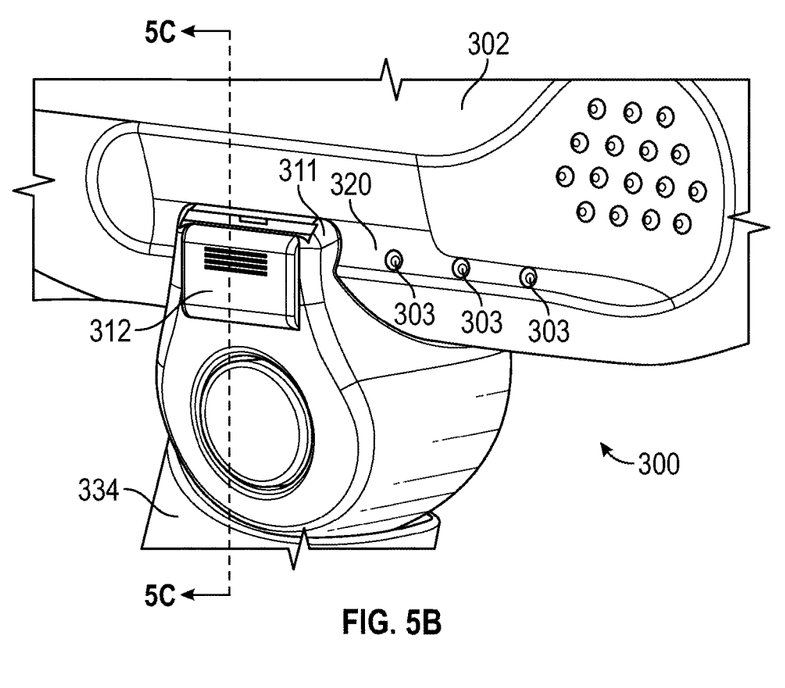
FIG. 5B is a side view of a handle paired to a debrider.

FIGS. 5A-5D show another example of a debrider handle. In some examples, a debrider 300 (as depicted in FIG. 5B) can include or use one or more longitudinal grooves 320 of a housing 302. The debrider 300 can have a pair of longitudinal grooves 320 running parallel on opposing side walls of the housing 302. A handle 334 can include or use one or more bars 311 sized and shaped to ride the one or more longitudinal grooves 320. Where the bars 311 of the handle 334 ride the grooves 320, the handle 334 can be slidingly paired to the housing 302. As such, the handle 134 can slide longitudinally along a length of the grooves 320. While the connection is described herein as having bars 311 riding grooves 320, other equivalent connections enabling longitudinal sliding motion of the handle 334 relative to the housing 302 are commonly known by persons skilled in the art and can be used herewith. For instance, alternatively or additionally the grooves 320 can be on the handle 334 and the bars 311 can be on the housing 302. FIG. 5A shows a perspective view of an example of the debrider handle 334. The handle 334 can include one or more bars 311 sized and shaped to conform to one or more grooves 320 of the housing 302. The one or more bars 311 can house one or more detent balls 345 sized and shaped to conform to one of a plurality of groove detents 303 (as shown in FIG. 5B) of the longitudinal grooves 320. The detents 345 can protrude medially from the bars 311. The handle 334 can also include or use one or more tabs 312. The one or more tabs can be located on the handle 334 at or near the one or more bars 311.

FIG. 5B shows a side view of an example of a portion of a handle paired to a portion of a debrider. The handle 334 can be slidably connected to the housing 302 where the bars 311 are sized and shaped to ride the grooves 320 of the housing. The longitudinal grooves 320 can include or use groove detents 303 sized and shaped to at least partially receive the one or more detent balls 345. In some examples, each longitudinal groove 320 can contain an amount of groove detents 303 within a range of 1 to 20 detents 303. Each longitudinal groove 320 can contain an amount of groove detents 303 within a range of 3 to 10 detents 303. When one or more of the detent balls 345 of the rails 311 are at least partially disposed in one or more of the plurality of groove detents 303, longitudinal movement of the handle 334 relative to the housing 302 can be restricted.

Figure 5C:
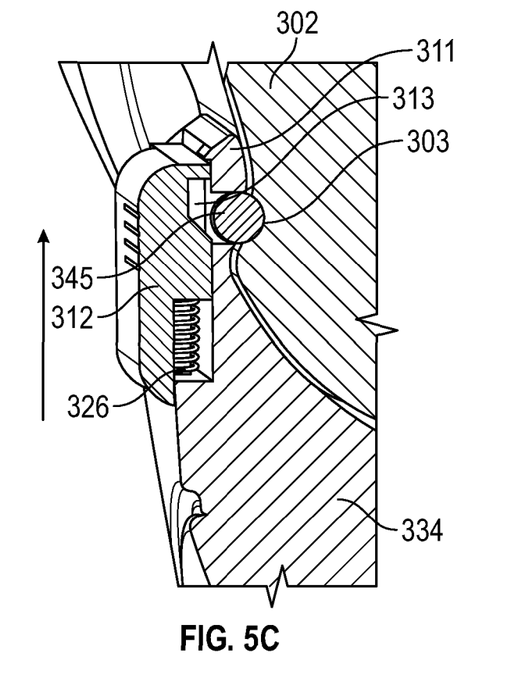
FIG. 5C is an isolated cross-section view of a debrider handle in a locked position.

FIG. 5C shows an isolated cross-section view of an example of a debrider handle in a locked position. Here, the cross-section view of the portion of the debrider 300 is taken along a plane 5C-5C as shown in FIG. 5B. The handle can include or use the tabs 312 located at or near the bars 311. Each of the one or more tabs 312 can include or use a tab detent 313. The handle 334 can be biased towards a locked position by one or more springs 326 located at or near the rails 311. The springs 326 can be fixed to the tabs 312. The springs 326 can bias the tabs 312 such that the tab detents are inaccessible by the detent balls 345. In one example, the springs can bias the tabs 312 distally towards the housing 302 and bias the tab detents 313 away from the detent balls 345 as they are housed in the rails 311. Where the tabs are biased to place the handle 334 in a locking position, the detent balls 345 can protrude medially towards the housing 302 and can be at least partially disposed within the plurality of groove detents 303 of the housing 302. While the handle 334 is in the locked position, the handle 334 can be fixed at one of several predetermined positions along the length of the housing 302.

Figure 5D:
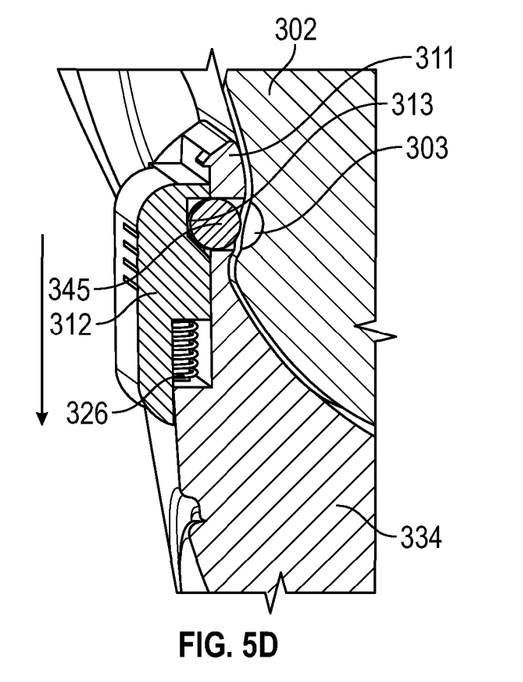
FIG. 5D is an isolated cross-section view of a debrider handle in an unlocked position.

FIG. 5D is an isolated cross-section view of a debrider handle in an unlocked position. Here, the cross-section view of the portion of the debrider 300 is taken along a plane 5C-5C as shown in FIG. 5B. The tabs 312 can be manually moved against the bias of the springs 326, as depicted. Moving the tabs 312 against the bias can move the tab detents 313 to become accessible by the detent balls 345. Where the detent balls 345 have access to the tab detents 313, they can be retracted away from the groove detents 303 towards the tab detents 313. Thus, in the unlocked position, the detent balls 345 can be removed from the groove detents 303 and sliding motion of the rails 311 riding the grooves 320 can be restored. It is understood that the bars 311, and the mechanisms contained within, could be alternatively configured to be located on the housing 302 and the grooves 320 on the handle.

In operation and use, a professional can provide or obtain a medical device 300 for use in debridement. The professional can manually move the one or more tabs 312 against their spring 326 bias to retract the detent balls 345 back into the handle. The professional can slide the one or more bars 311 along the one or more grooves 320 to slidingly attach the handle 334 to the housing 302. The professional can place the handle 334 at a desired, predetermined position and release the tabs 312 to lock the handle in place. In one example, the professional can use this handle for debridement with "pistol grip". In another example, the professional can manually move the tabs 312 against their bias to the unlocked position and can slidably remove the handle 334 from the housing 302 and use the device in "pen grip". The professional can position the cutter 104 relative to the surgical site 140, and sever, cut, shave, drill, and/or remove tissue or other objects therefrom.

Figure 6A:
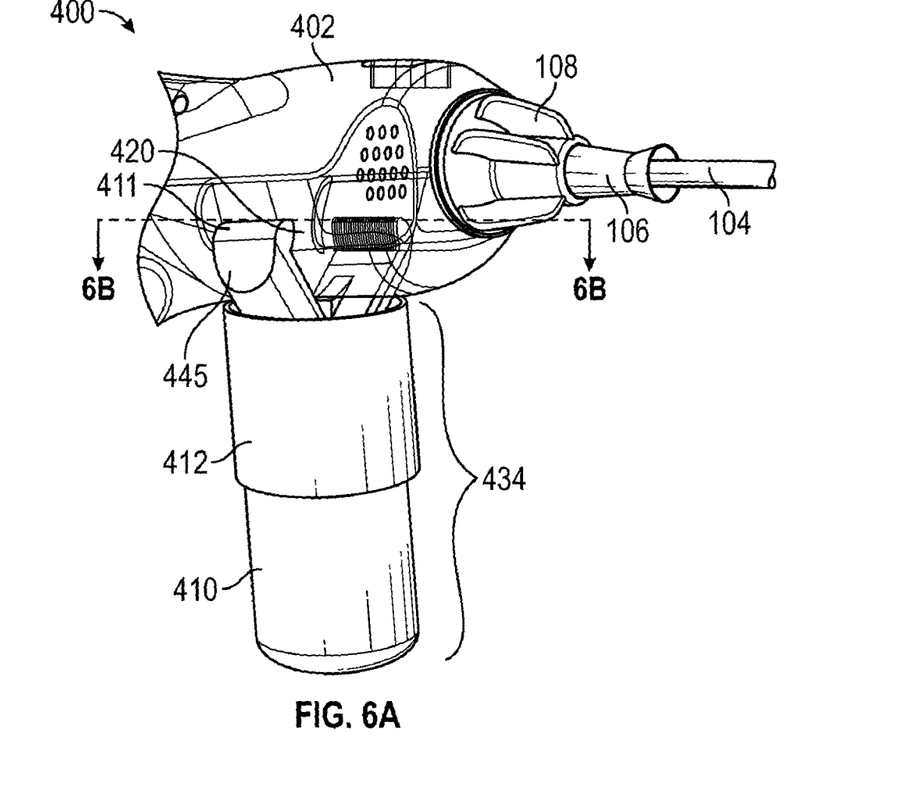
FIG. 6A is a perspective view of a handle paired to a debrider.
Figure 6B:
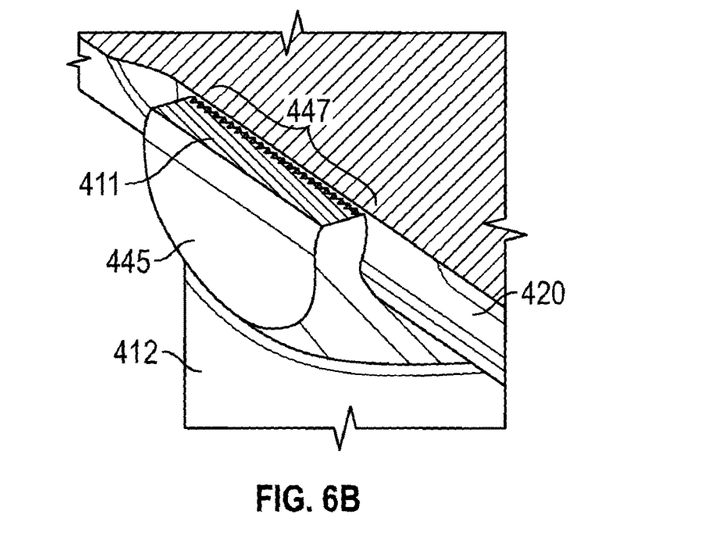
FIG. 6B is an isolated view of a handle paired to a debrider.

FIGS. 6A-6D show yet another example of a debrider handle. FIG. 6A depicts a portion of a debrider 400 in phantom as it is paired with a handle 434. The debrider 400 can be paired to the handle 434 which can include or use a handle base 410, a sleeve 412 and a pair of jaws 445 each having bars 411 sized and shaped to conform to grooves 430 of a housing 402. FIG. 6B shows a cross-section view of a portion of a debrider taken along a plane 6B-6B as shown in FIG. 6A. The bars 411 can have a sticky or tacky surface finish, knurling, or serrations (as depicted in FIG. 6B) such as to increase friction between the bars 411 and the grooves 420. Alternatively or additionally, the grooves 420 can have a sticky or tacky surface finish, knurling, or serrations. The pair of jaws can be hingedly connected to the handle base about a pivot 418. The pivot 418 can be a pin, rod, or other substantially cylindrical portion extending through the jaws 445 and the handle base 410. The pivot 418 can also be a physical, rotatable connection between the body of the handle base 410 and the jaws 445. The pivot 418 can also be one or more projections on the jaws 445 which can mate with one or more apertures on the handle base 410. The pivot 418 can also be one or more projections on the handle base 410 which can mate with one or more apertures on the jaws 445. The jaws 445 can intersect about the pivot 418 such as to create a vertical pair of jaw angles: an inferior jaw angle 446 and a superior jaw angle 444. The jaws can both be attached to a jaw spring 427 at or near the inferior angle 446. The jaw spring 427 can bias the jaws laterally at both the inferior jaw angle 446 and superior jaw angle 444. Thus, the above described jaw configuration can function to spread the jaws apart, creating a relatively wide vertical pair of jaw angles 446 and 444.

Figure 6C:
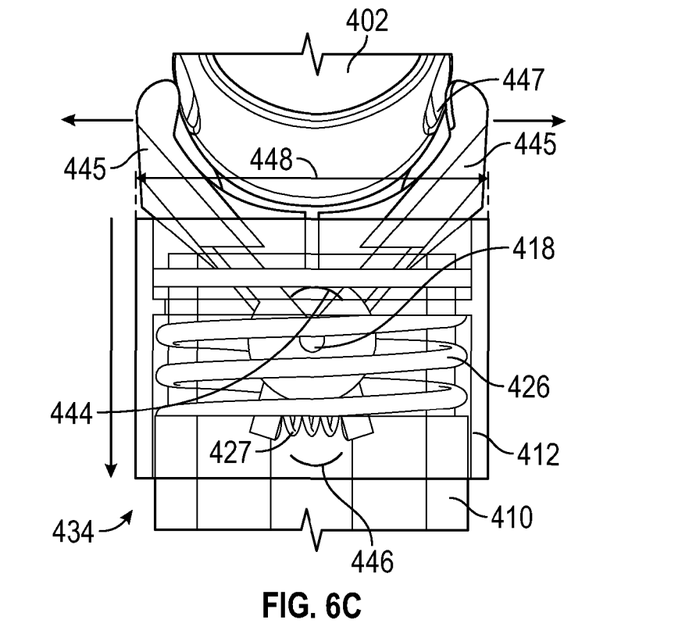
FIG. 6C is a front view of a debrider handle in an unlocked position.
Figure 6D:
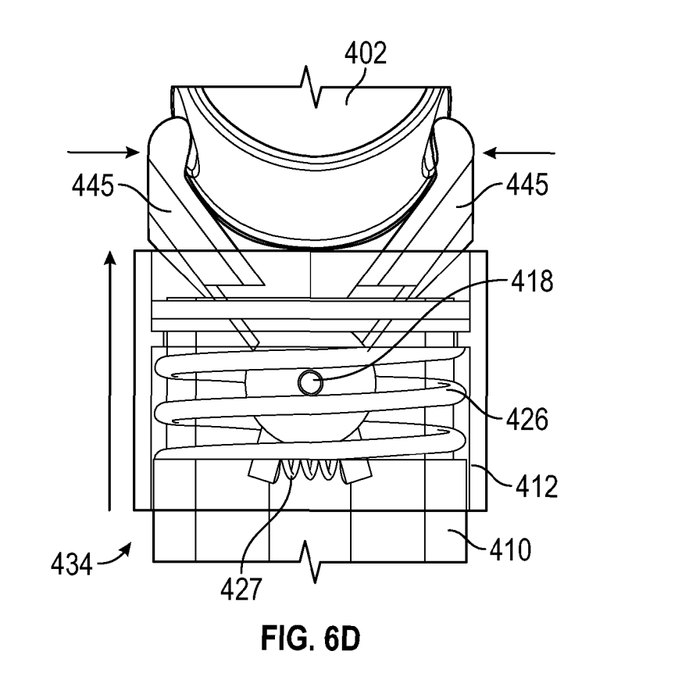
FIG. 6D is a front view of a debrider handle in a locked position.

The sleeve 412 can be a tube and can be sized and shaped such as to slidably couple to an outer diameter of the handle base 410. The sleeve 412 is shown in phantom in FIGS. 6C & 6D in order to depict the other components therein. The sleeve 412 can further be sized and shaped such that the inner diameter of the sleeve 412 is smaller than a jaw width 448 (as depicted in FIG. 6C) when clamped to a housing 402. The sleeve 412 and handle base 410 can be attached to a sleeve spring 426. The sleeve spring can bias the sleeve 412 to slide upward distally from the handle base. In doing so, the inner diameter of the sleeve 412 can clamp the jaws 445 such as to move the jaws medially against the bias of the jaw spring 427. The sleeve spring 426 can have a significantly higher spring force than that of the jaw spring 427. Thus, the sleeve spring 426 can cause the mechanism to overcome the bias of the jaw spring 427 except where manual pressure is exerted on the mechanism against the direction of the sleeve spring 426. A professional can exert such manual pressure on the sleeve 412 in a superior direction in order to move the handle 434 to an unlocked position as depicted in FIG. 6C. In the unlocked position, the jaws 445 are at least partially released by the sleeve 412 allowing the vertical pair of jaw angles 446 and 444 in increase. The professional can return the handle 434 to locking position by releasing the sleeve 412, allowing it to return to its bias as depicted in FIG. 6D.

Figure 7A:
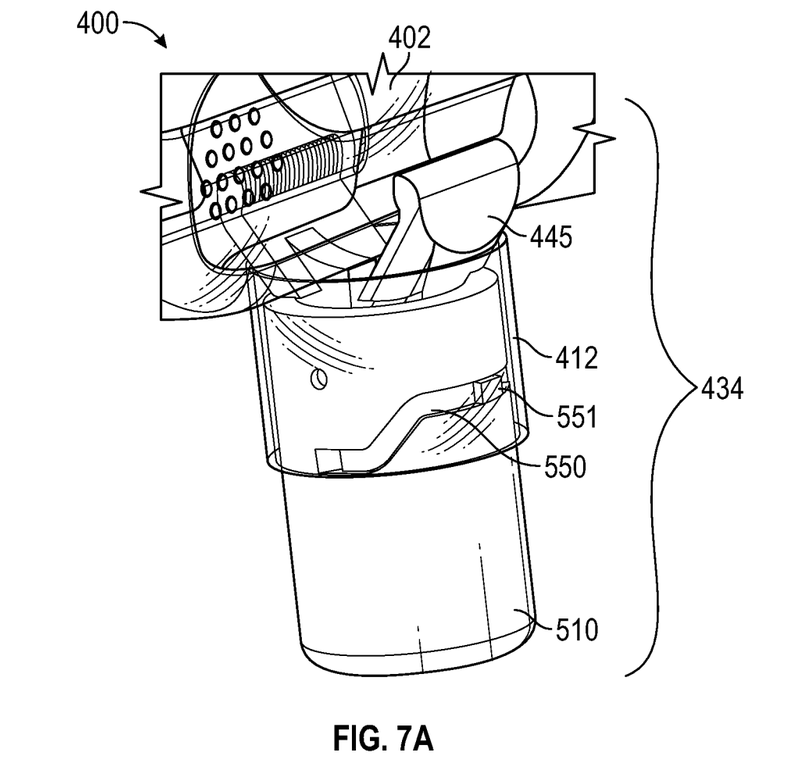
FIG. 7A is a perspective view of a debrider handle in a locked position.
Figure 7B:
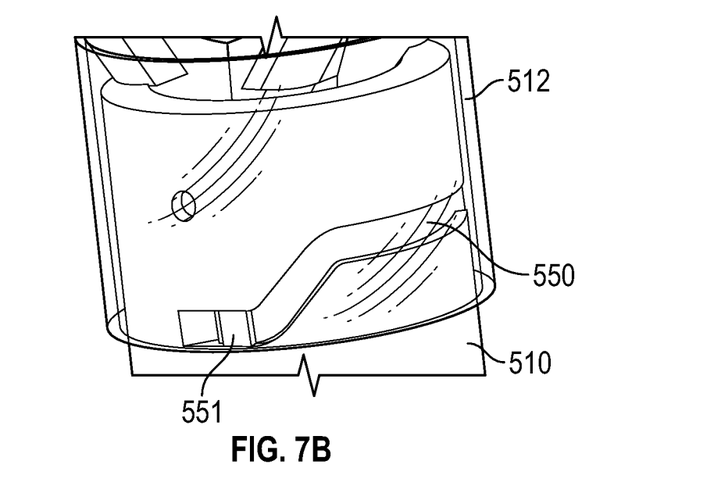
FIG. 7B is an isolated view of a debrider handle in an unlocked position.

In another example, as depicted in 7A and 7B, the sleeve 412 can include or use a channel mechanism to supply the superior clamping pressure. FIG. 7A depicts a portion of the debrider 400 in phantom as it is paired with a handle 434. FIGS. 7A & 7B also show the sleeve 412 in phantom in order to depict the contents therein. The channel mechanism can include or use a channel 550 and a follower 551. The channel 550 can be included in the handle base 410 and the follower 551 can be included in the sleeve 412. Alternatively, the channel 550 can be included in the sleeve 412 and the follower 551 can be included in the handle base 410. Manually turning the sleeve 412, such as turning the sleeve 412 clockwise in accordance with FIG. 7A, can cause the sleeve 412 to slide upward distally from the handle base 110. The sleeve 412, channel 550, and follower 551 can alternatively be configured such as to allow for counter-clockwise turning to cause the sleeve 412 to slide upward distally from the handle base 110. The channel 550 can include or use inclined segments, horizontal segments, or both. The channel 550 can be s-shaped such as to allow for a horizontal, unlocked position, a vertical rise position, and a horizontal, locked position. Other appropriate shapes and configurations of a channel 550 and a follower 551 can also be used. The sleeve 412 can be turned in an opposite direction to move the sleeve 412 in an inferior direction, releasing the clamping pressure on the jaws 445, as depicted in FIG. 7B.

In operation and use, a professional can provide or obtain a medical device 400 for use in debridement. The professional can manually move the sleeve 412 in an inferior direction to release clamping pressure on the jaws. The professional can slide the one or more bars 411 along the one or more grooves 420 to slidingly attach the handle 434 to the housing 402. The professional can place the handle 434 at a desired, predetermined position and release or turn the sleeve 412 to cause the sleeve 412 to move in a superior direction, clamping the jaws 445 and locking the handle 434 to the housing 402. In one example, the professional can use this handle for debridement with "pistol grip". In another example, the professional can manually move the sleeve 412 in an inferior direction to the unlocked position and can slidably remove the handle 434 from the housing 402 and use the device in "pen grip". The professional can position the cutter 104 relative to the surgical site 140, and sever, cut, shave, drill, and/or remove tissue or other objects therefrom.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein. In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A medical device for tissue removal, the medical device comprising:
    an elongate housing;
    a shaft extending through the elongate housing and distally therefrom, the shaft including a cutter configured to sever tissue;
    a drive configured to rotate the cutter, reciprocate the cutter, or both;
    a handle slidably coupled to the elongate housing and extending laterally therefrom; and
    at least one locking mechanism configured to fix the handle to the elongate housing at a plurality of different longitudinal positions along the elongate housing;
    wherein the handle is slidably coupled to at least one longitudinal groove of the elongate housing;
    wherein the handle is configured to provide:
    an unlocked position wherein the handle slides within the at least one longitudinal groove; and
    a locked position wherein the at least one locking mechanism applies pressure to the elongate housing, the pressure restricting travel of the handle relative to the elongate housing;
    wherein the at least one locking mechanism comprises a moveable element slidable within a bore of the handle, the moveable element configured to protrude from the bore distally towards the elongate housing and apply pressure thereto; and
    wherein the moveable element is configured to be manipulated by a lever mechanism to protrude from the bore.

2. A medical device for tissue removal, the medical device comprising:
    an elongate housing;
    a shaft extending through the elongate housing and distally therefrom, the shaft including a cutter configured to sever tissue;
    a drive configured to rotate the cutter, reciprocate the cutter, or both;
    a handle slidably coupled to the elongate housing and extending distally therefrom; and
    at least one locking mechanism configured to fix the handle to the elongate housing at a plurality of different longitudinal positions along the elongate housing;
    wherein the handle is slidably coupled to at least one longitudinal groove of the elongate housing;
    wherein the handle is configured to provide:
    an unlocked position wherein the handle slides within the at least one longitudinal groove; and
    a locked position wherein the at least one locking mechanism applies pressure to the elongate housing, the pressure restricting travel of the handle relative to the elongate housing;
    wherein the at least one locking mechanism comprises a moveable element slidable within a bore of the handle, the moveable element configured to protrude from the bore distally towards the elongate housing and apply pressure thereto; and
    wherein the at least one longitudinal groove includes a t-shaped slot.

3. The medical device of claim 2, wherein a t-shaped nut is attached at a protruding end of the moveable element, the t-shaped nut configured to apply pressure to the t-shaped slot upon manipulation of the moveable element by a cam.

4. The medical device of claim 2, wherein the at least one locking mechanism is configured to apply medial pressure on two or more longitudinal grooves of the elongate housing.

5. A medical device for tissue removal, the medical device comprising:
    an elongate housing, defining a central longitudinal instrument axis;
    an instrument shaft extending, along the longitudinal axis, through the elongate housing and distally therefrom;
    a handle sized and shaped to slidably interface with the elongate housing and extend laterally from the elongate housing; and
    at least one handle locking mechanism configured to fix the handle to the elongate housing at a specified longitudinal position of the elongate housing and along the longitudinal axis;
    wherein:
    the handle includes a tongue feature configured to slidably interface with a longitudinal groove of the elongate housing;
    at least one of the tongue feature or the longitudinal groove include a t-shaped cross-sectional profile; and
    the at least one handle locking mechanism is configured to selectively apply pressure toward an interior side of a lip of the elongate housing to secure the handle to the elongate housing.

6. The medical device of claim 5, wherein the at least one handle locking mechanism comprises a rod moveable within a bore of the handle, the rod configured to protrude from the bore toward the elongate housing and apply pressure thereto.

* * * * *